US005792625A

United States Patent [19]
Klaenhammer et al.

[11] Patent Number: 5,792,625
[45] Date of Patent: Aug. 11, 1998

[54] BACTERIOPHAGE-TRIGGERED CELL SUICIDE SYSTEMS AND FERMENTATION METHODS EMPLOYING THE SAME

[75] Inventors: Todd R. Klaenhammer, Raleigh; Mark A. Conkling, Fuquay-Varina, both of N.C.; Dan O'Sullivan, Minneapolis, Minn.; Gordana Djordjevic, San Diego, Calif.; Shirley A. Walker, Raleigh, N.C.; Christopher G. Taylor, St. Charles, Mo.

[73] Assignee: North Carolina State University, Raleigh, N.C.

[21] Appl. No.: 709,616

[22] Filed: Sep. 9, 1996

Related U.S. Application Data

[63] Continuation-in-part of Ser. No. 709,520, Sep. 6, 1996, abandoned.

[51] Int. Cl.⁶ ............................ C12N 1/21; C12N 15/11; C12N 21/00; C12N 1/00
[52] U.S. Cl. .................. 435/69.1; 435/71.1; 435/172.3; 435/252.3; 435/252.33; 435/320.1; 536/23.1; 536/23.2; 536/24.1
[58] Field of Search ................ 435/252.3, 252.33, 435/172.3, 520.1, 69.1, 71.2; 536/23.1, 23.2, 24.1

[56] References Cited

PUBLICATIONS

Gerdes et al., Proc. Natl. Acad. Sci. USA, 83:3116–3120, May 1986.
Yu et al., Proc. Natl. Acad. Sci. USA, 91:802–806, Jan. 1994.
Strittmatter et al., Biotechnology 13:1085–1089, Oct. 1995.
Dinsmore et al., Molecular Biotechnology, 4:297–314, 1995.

*Primary Examiner*—Johnny F. Railey, III
*Attorney, Agent, or Firm*—Myers Bigel Sibley & Sajovec

[57] ABSTRACT

Described herein is a bacterial cell containing a recombinant bacteriophage defense mechanism. The defense mechanism comprises a bacteriophage promoter (e.g., a phage φ31 promoter; a T7 promoter) operatively associated with a heterologous DNA encoding a product lethal to the bacterial cell. The bacterial cell is susceptible to infection by a bacteriophage, and the promoter is activated upon the infection of said bacterial cell by that bacteriophage. Bacteria useful in carrying out the invention include both gram negative and gram positive bacteria (e.g., *Lactococcus lactis*; *Escherichia coli*); the heterologous DNA may encode an enzyme that degrades nucleic acid (e.g., the products of the LlaI restriction cassette; barnase). Recombinant DNAs useful for making the foregoing cells, cultures prepared from such cells, and fermentation methods carried out with such cells are also disclosed.

22 Claims, 7 Drawing Sheets

FIG. 2A

5' GATCCGGATGTTATAAACAAAATCCACTAGCAGAGCATTGTAAGGTTGGTTGGTATTCCAGT
TACAGAGAGATATTGAAGAACATTTTACAAAAATGATGAATCTAAAGATGTATTAATGCC
AGATAATAACAAAAAGCCCACTGCAATGGGCTTAAAACAGATTCTTAACTACTATTA
TATCATAAATATAAGGAGTTGAGACACTATGAGTAGAAGATATAACCTTACTGACAGCGACTT
GAAAGCTATAGAGAAGAAGAGCTCTTTATGTGTCAACATGACCACCGCTATCAATATCGCAA
GTATGAGTAGAAGTAAACAATCACATGATATAATGTAGGTGCGTGGTAGTCAAGTATAAT
CTCAAAGCCAGTAGAACCGAATCAATGAGTACAAGATTGGTTGGAGATGCTGACATAACTCCAAAGTCTATA
TGAGTTAAGAACCGAATCAATGAGTACAAGATTGGTTGGAGATGAAGATATGCAATT
GGTATTCCACTACCGTGTATCGGTAAACGTATACAGTACCAGAGATAGCTGATAA|GTGT 566

CACACAATAACTGAGCGCCAATACTTTAGAAGAGAAGCAATACTTGAGAAGTATGATGAGAT
ATGTGACGGCTCTGGTAATTGTCACCCTTTGGGCGAAACTGACAAGATAAATGTGTATTA
TAGTATCATCAAATAAAACAAATAAAGCCAGCGGATATATTCTGTTGGCTTTTGTGTGGAGA
                                                    804
AAGTGAGGTGACCTCCCATAGCATTACGTGCTGACCGTACTGGTGC|
                                              GCATCGTGTAGCCCTTTG
ATAAGAATAGAAAGATTCTTTAAAGACACAGAACACTTGTGGAATATGTGGCAAGCCAATC
GGATC 888 3'

BACTERIOPHAGE-TRIGGERED CELL SUICIDE SYSTEMS AND FERMENTATION METHODS EMPLOYING THE SAME

RELATED APPLICATIONS

This application is a continuation-in-part of the commonly owned, application by Todd R. Klaenhammer, Mark Conkling, Dan O'Sullivan, Gordana Djordjevic, Shirley Walker, and Christopher G. Tailor titled "Bacteriophage-Triggered Cell Suicide Systems and Fermentation Methods Employing the Same", application Ser. No. 08/709,520, filed Sep. 6, 1996, now abandoned the disclosure of which is incorporated by reference herein in its entirety.

This invention was made with Government support under NRICGP/USDA Project No. 92-37500-8018. The Government has certain rights to this invention.

FIELD OF THE INVENTION

This invention relates to fermentations in general, and particularly relates to methods and products useful for imparting bacteriophage resistance to fermentations.

BACKGROUND OF THE INVENTION

Many important industrial bioprocesses and food fermentations are susceptible to attack by bacteriophages. Control of phage problems in the commercial arena requires preventing phage contamination, employing strains that are resistant to phage infection, and minimizing opportunities for the appearance of new virulent phages. With the diversity of fermentation systems, it is not always possible to operate an aseptic fermentation or, if available, maintain its integrity. Therefore, the longevity of any highly specialized strain in a commercial situation depends on the bacterium's relative phage resistance or sensitivity and how quickly defiant phages appear and proliferate against it. Modern biotechnology continues to provide increasing opportunities to create specialized strains with valuable processing or product characteristics. In dairy fermentations, which are plagued by phage attacks more often than any other bioprocessing industry, this problem has been traditionally approached with varying success by isolating phage-resistant mutants and incorporating the derivatives into the starter culture formulations. Over the last decade, a number of naturally occurring plasmid-encoded defenses have been discovered in Lactococcus species which prevent phage adsorption, prevent DNA injection, restrict unmodified phage DNA by resident restriction and modification (R/M) systems, or abort the phage infection following the early stages of phage development (C. Hill, FEMS Microbiol. Rev. 12: 87–108 (1993); T. Klaenhammer and G. Fitzgerald, in M. J. Gasson and W. M. de Vos (eds.), *Genetics and biotechnology of lactic acid bacteria*. p. 106–168 (Blackie Academic and Professional, Glasgow, U.K. 1994)).

Using conjugation or electrotransformation approaches, phage defenses can now be genetically introduced to bioprocessing strains by pyramiding selected defense systems (T. Klaenhammer, *Food Diotechnol.*, 19: 675–682 (1991); E. Durmaz and T. Klaenhammer, *Appl. Environ. Microbiol.* 61: 1266–1273 (1995)). Bacteria which are recalcitrant to phage infection can be derived. After extended use, however, new virulent phages inevitably appear against new or improved strains as selection pressures compromise defenses or the phages define genetic routes to circumvent them (C. Hill et al., *J. Bacteriol.* 173: 4363–4370 (1991); S. Moineau et al., *Appl. Environ. Microbiol.*, 59: 197–202 (1993)).

It is the rare appearance and then unchecked proliferation of new virulent phages that threaten most fermentation industries. Phage protection strategies not only should provide resistance, but also design mechanisms that will capture an emerging phage and prevent its proliferation to disruptive population levels (W. Sing and T. Klaenhammer, *J. Gen. Microbiol.* 136: 1807–1815 (1990); T. Klaenhammer, *Food Biotechnol.*, 19: 675–682 (1991)). Diverse pathways exist for the cell to halt phage development post infection, leading concurrently to cell death. The variety of abortive infection (Abi) systems illustrates the importance of these natural mechanisms that limit phage proliferation. Essentially, Abi mechanisms are recognized as natural self-imposed suicide systems that limit phage development. It appears that cell death occurs as an aftermath of lasting infection after the host machinery has been redirected irreversibly towards phage functions.

SUMMARY OF THE INVENTION

Rather than directing defense against phage per se, we herein describe a system wherein a phage-specific inducible promoter is employed to sense the infection and trigger expression of a gene designed to kill the host and thereby kill infecting phage. Sacrificing infected cells through phage-induced suicide strategies establishes an altruistic goal of protecting the bacterial population as a whole by enticing new virulent phages into individual cells armed with genetic traps that destroy the potential of the infecting phage and bacterial host to proliferate new progeny phages.

In view of the foregoing, a first aspect of the present invention is a bacterial cell containing a recombinant bacteriophage defense mechanism. The defense mechanism comprises a bacteriophage promoter (e.g., a phage $\phi$31 promoter; a T7 promoter) operatively associated with a heterologous DNA encoding a product lethal to the bacterial cell. The bacterial cell is susceptible to infection by a bacteriophage, and the promoter is activated upon the infection of said bacterial cell by that bacteriophage. Bacteria useful in carrying out the invention include both gram negative and gram positive bacteria (e.g., *Lactococcus lactis*; *Escherichia coli*); the heterologous DNA may encode an enzyme that degrades nucleic acid (e.g., the products of the LlaI restriction cassette; barnase).

A second aspect of the present invention is a method of fermenting a substrate to produce a product. The method comprises combining a fermentation medium and bacteria as described above, and then fermenting the fermentation medium with the bacteria to produce the product.

A third aspect of the present invention is a fermentation starter culture comprising a plurality of bacterial cells containing a recombinant bacteriophage defense mechanism as described above. The starter culture may be a defined culture, and in one embodiment is a pure culture. Cultures useful for fermenting food, such as milk, are one embodiment of the invention.

A fourth aspect of the present invention is a recombinant DNA comprising a bacteriophage promoter operatively associated with a heterologous DNA encoding a product lethal to a bacterial cell.

The foregoing and other objects and aspects of the present invention are explained in detail in the drawings herein and the specification set forth below.

BRIEF DESCRIPTION OF THE DRAWINGS

FIG. 2A shows the nucleotide sequence of the 888 bp φ31 fragment (SEQ ID NO: 1) exhibiting both constitutive and phage-inducible promoter activity. The phage-inducible promoter is represented by the bosed region (nucleotides 566–804).

FIG. 3A shows growth curves for *L. lactis* NCK690 (●) and *L. lactis* NCK690 (pTRK414H) (□) in the absence of phage φ31.

FIG. 3B shows growth curves of *L. lactis* NCK690 infected with 10⁷ (filled triangle with apex down), 10⁶ (filled triangle with apex up), and 10⁵ (filled diamond) pfu/ml of phage φ31.

FIG. 5A shows the growth curves of *L. lactis* NCK690 in the absence of phage (filled square; control) and when infected with 10⁷ pfu/ml of phages: φ31 (filled circle; control), φ31.1 (filled triangle with apex up), and φ31.8 (filled triangle with apex down).

FIG. 5B shows the growth curves of *L. lactis* NCK690 (pREK414H) when infected with 10⁷ pfu/ml of phages: φ31 (open circle; control), φ31.1 (open triangle with apex up), and φ31.8 (open triangle with apex down).

DETAILED DESCRIPTION OF THE INVENTION

Figure 1A:
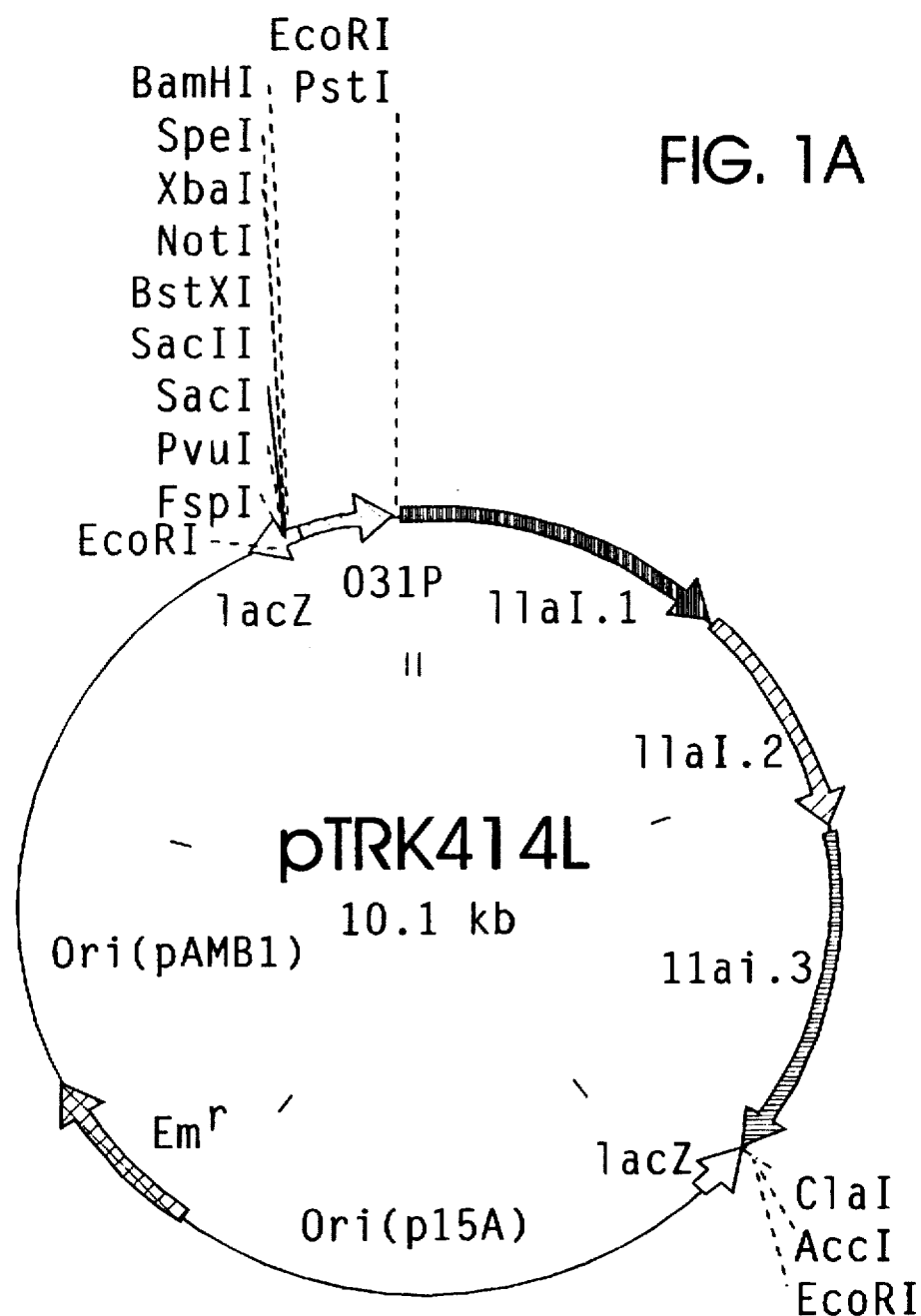
FIG. 1 shows the pTRK414L (low copy) and pTRK414H (high copy) plasmids encoding the $\phi$031P/LlaIR+–based bacterial suicide cassette. The llaI.1, llaI.2, and llaI.3 genes encode the restriction endonuclease activity of the LlaI r/M system; φ31P: the 239 base pair FspI-BamHI phage DNA fragment from pTRK391 that encodes a phage φ31-specific middle, trigger promoter; Ori(pAMβ1): gram-positive replication origin; Ori(p15A): gram-negative replication origin; Em: erythromycin resistance gene; lacZ: β-galactosidase gene that allows blue/white selection in α-complementing *Escherichia coli* strains (only flanking 5' and 3' sequences of the gene are present on pTRK414L and pTRK414H vectors). Only relevant restriction sites are shown.

A phage-inducible suicide system useful for fermentation methods requires an appropriate death gene, a phage-inducible promoter triggered only after phage infection (i.e., not constitutively active in the bacterial cell or activated by stimuli other than those presented by bacteriophage), and a suitable vector that provides adequate copies of the suicide cassette in the bacterial host.

A. BACTERIOPHAGE PROMOTERS

Numerous inducible phage promoters that are not expressed by the bacteria in the absence of a phage infection are available. Many such promoter elements are responsible for temporal expression and have been described in well characterized bacteriophages attacking *E. coli* and *Bacillus subtilis* (Lee and Pero, (1981); Dunn and Studier, 1983; Elliot and Geiduschek, 1984; Kassavetis et al., 1986). However, only one inducible element has been characterized to date for a lytic lactococcal bacteriophage. A middle, phage-inducible promoter from the P335 species lactococcal bacteriophage φ31 was initially cloned on a 888-bp fragment (SEQ ID NO: 1) (D. O'Sullivan et al., *Bio/Technol.* 14: 82–87 (1996)). Molecular characterization and primer extension analysis of the promoter-containing region revealed four transcription sites, two of which were strictly inducible after infection of *L. lactis* with phage φ31 (S. Walker et al., *J. Dairy Sci.* 78, 108 (1995)). As described below, a 239-bp fragment was subcloned containing two tandem transcription starts that are expressed only after phage infection. The suicide system was assembled by placing the phage φ31-specific, trigger promoter (designated φ31P) 5' of the LlaIR+ cassette.

Additional sources of bacteriophage promoters useful for carrying out the present invention include phage φT3 (Morris et al., *Gene* 41: 193–200 (1986)), phage φSP6 (Butler and Chamberlin, *J. Biol. Chem.* 257: 5772–5778 (1982)), phage φT4 (Geiduschek and Kassavetis, in *The Bacteriophages* pp. 93–115 (R. Calendar, Ed. 1988)), phage φSP (Talkington and Pero, *Proc. Natl. Acad. Sci. USA* 76: 5465–5469 (1978)) and phage φ29 (Monsalve et al., *Virology* 207: 23–31 (1995)).

As indicated above, the promoter employed should be a phage-inducible promoter. This is, the promoter should be normally silent, or should not be a constitutively active promoter (i.e., have insufficient constitutive activity to activate transcription of the DNA encoding the product lethal to the bacterial cell to an extent sufficient to kill the cell in the absence of phage infection). Promoters that possess constitutive activity may be modified so that they are phage-inducible promoters, as described herein.

Any suitable vector may be used to carry out the present invention, including both plasmid vectors and cassettes inserted into the bacterial genome by recombinant techniques. Copy number of the vector is not critical, and may be adjusted as necessary in light of the choice of the particular DNA encoding the lethal product, and the sensitivity of the particular bacterial cell thereto.

B. DNA ENCODING PRODUCTS LETHAL TO BACTERIAL CELLS

Heterologous DNAs employed in carrying out the present invention encode a product which is lethal to bacterial cells. A wide variety of protein or peptide products that are lethal to bacterial cells can be used, including (but not limited to) enzymes capable of degrading nucleic acids (DNA, RNA) such as nucleases, restriction endonucleases, micrococcal nuclease, RNase A, RNase CL-3, RNase T1, and barnase; enzymes that attack proteins such as trypsin, pronase A, carboxypeptidase, endoproteinase Asp-N, endoproteinase Glu-C, cellulase with an export signal, and endoproteinase Lys-C; toxins from plant pathogenic bacteria such as phaseolotoxin, tabtoxin, and syringotoxin; lipases such as produced from porcine pancrease and Candida cyclindracea, membrane channel proteins such as glp F and connexins (gap junction proteins, and antibodies that bind proteins in the cell so that the cell is thereby killed or debilitated. Genes which produce antibodies to bacterial cell proteins can be produced as described in W. Huse et al., *Science* 246, 1275–1281 (1989). Proteins to which such antibodies can be directed include, but are not limited to, RNA polymerase, respiratory enzymes, cytochrome oxidase, Krebs cycle enzymes, protein kinases, and aminocyclopropane-1-carboxylic acid synthase. Additional products lethal to bacterial cells that may be used in carrying out the present invention are discussed below.

Particularly preferred is a structural gene encoding mature *Bacillus amyloliquefaciens* RNase (or Barnase). See, e.g., C. Mariani et al., *Nature* 347, 737–741 (1990); C. Paddon and R. Hartley, *Gene* 40, 231–39 (1985). It is preferred, particularly where the bacteria is employed in the fermentation of a food product, that the bacteria-lethal product of the heterologous DNA is non-toxic to animals, and particularly is non-toxic to mammals, including humans.

C. FERMENTATIVE BACTERIA

The art of fermentation is well known and the instant method is useful in a wide variety of fermentation processes. In a preferred embodiment of the present invention, the instant method relates to bacteria capable of fermenting food substrates, and more particularly milk.

Bacteria capable of fermenting foods include those bacteria used in any type of food fermentation, including, but not limited to, the fermentation of milk, egg, meat, fruit, vegetables, and cereals. See generally Food Biotechnology, (D. Knorr Ed. 1987) (Marcel Dekker, Inc.); Fermented Foods (A. Rose Ed. 1982)(Academic Press); C. Pederson, Microbiology of Fermented Foods, (2d ed. 1979)(AVI Publishing Co.).

Bacteria used for the fermentation of meat (including beef, pork, and poultry) include, but are not limited to, lactic acid bacteria, *Pediococcus cerevisiae*, *Lactobacillus plantarum*, *Lactobacillus brevis*, *Micrococcus species*, *Leuconostoc citrovorum*, *Leuconostoc citrovorum*, and mixtures thereof. See Food Biotechnology, 538–39 (D. Knorr Ed. 1987); C. Pederson, *Microbiology of Fermented Foods*, 210–34 (2d ed. 1979); U.S. Pat. No. 2,225,783 to Jensen and Paddock.

Bacteria used for the fermentation of vegetables (e.g., carrots, cucumbers, tomatoes, peppers, and cabbage) include, but are not limited to, *Lactobacillus plantarum*, *Lactobacillus brevis*, *Leuconostoc mesenteroides*, *Pediococcus pentosaceus*, and mixtures thereof. See Food Biotechnology, 540 (D. Knorr Ed. 1987); C. Pederson, Microbiology of Fermented Foods, 153–209 (2d ed. 1979); U.S. Pat. No. 3,024,116 to Engelland; U.S. Pat. No. 3,403,032 to Etchells et al.; U.S. Pat. No. 3,932,674 to Etchells et al.; U.S. Pat. No. 3,897,307 to Porubcan et al.

Bacteria used in the fermentation of dough formed from cereals (e.g., wheat, rye, rice, oats, barley, and corn) include yeasts such as *Saccharomyces cerevisiae* and *Candida utilis*; and lactic acid bacteria of the genera Lactobacillus, Lactococcus, Pediococcus and Leuconostoc, including, but not limited to *Lactobacillus delbrueckii*, *Lactobacillus debreuckii* subsp. leichmanni, *Lactobacillus plantarum*, *Lactobacillus casei*, *Lactobacillus brevis*, *Lactobacillus fermenti*, *Lactobacillus pastorianus*, *Lactobacillus buchneri*, and *Leuconostoc mesenteroides*. See generally Food Biotechnology, 235–70 (D. Knorr Ed. 1987); U.S. Pat. No. 3,734,743 to Kline and Sugihara; U.S. Pat. No. 3,681,083 to Everson; U.S. Pat. No. 3,993,783 to Khoudokormoff and Langejan; U.S. Pat. No. 3,843,800 to Langejan; U.S. Pat. No. 3,410,692 to Wutzel.

Wine is produced by the fermentation of fruit juice, typically grape juice, with yeasts, such as *Saccharomyces cerevisiae* and *Saccharomyces ellipsoideus*, as well as with a broad variety of lactic acid bacteria including *Pediococcus pentosaceus*, *Lactobacillus plantarum*, *Leuconostoc mesenteroides*, *Leuconostoc dextranicum*, *Leuconostoc cremoris*, *Lactobacillus brevis*, and *Lactobacillus fermenti*. Beer is produced by the fermentation of malt with yeasts such as *Saccharomyces cerevisiae* and *Saccharomyces carlsbergensis*. See C. Pederson, Microbiology of Fermented Foods, 271–309 (2d ed. 1979).

Milk is fermented to produce products such as cheese, yoghurt, kefir, and acidophilus milk. Cheese fermentation bacteria are discussed separately below. Otherwise, bacteria used for the fermentation of milk include, but are not limited to, Lactobacillus debreuckii subsp. bulgaricus, *Lactobacillus acidophilus*, *Streptococcus salivarius* subsp. thermophilus, and mixtures thereof. See Food Biotechnology, 530 (D. Knorr Ed. 1987); C. Pederson, Microbiology of Fermented Foods, 105–35 (2d ed. 1979).

Bacteria used for the fermentation of milk to produce cheese include, but are not limited to, *Lactobacillus bulgaricus*, *Lactobacillus helveticus*, *Streptococcus salivarius* subsp. thermophilus, *Lactococcus lactis* subsp. lactis, *Lactococcus lactis* subsp. cremoris, *Lactococcus lactis* subsp. lactis biovar. diacetylactis, and mixtures thereof. See Food Biotechnology, 530 (D. Knorr Ed. 1987); C. Pederson, Microbiology of Fermented Foods, 135–51 (2d ed. 1979).

Bacteria used for the fermentation of egg include *Pediococcus pentosaceus*, *Lactobacillus plantarum*, and mixtures thereof. See Food Biotechnology, 538–39 (D. Knorr Ed. 1987).

In a particularly preferred embodiment, the present invention is employed for the fermentation of milk with the lactococci (previously classified as the group N Streptococci), such as *Lactococcus lactis* subsp. lactis, *Lactococcus lactis* subsp. cremoris, and *Lactococcus lactis* subsp. lactis biovar. diacetylactis.

While the present invention is, in one embodiment, directed to the fermentation of food, the invention may be practiced with any process involving fermentative bacteria susceptible to disruption by bacteriophage infection, including but not limited to processes for the production of antibiotics, amino acids, and solvents. Products produced by fermentation which are known to have encountered bacteriophage infection, and the corresponding infected fermentation bacteria, include Cheddar and cottage cheese (*Lactococcus lactis*, *Lactococcus cremoris*), Yogurt (*Lactobacillus bulgaricus*, *Streptococcus thermophilus*), Swiss cheese (*S. thermophilus*, *Lactobacillus lactis*, *Lactobacillus helveticus*), Blue cheese (*Leuconostoc cremoris*), Italian cheese (*L. bulgaricus*, *S. thermophilus*), Viili (*Lactococcus cremoris*, *Lactococcus lactis* subsp. diacetylactis, *Leuconostoc cremoris*), Yakult (lactobacillus casei), casein (*Lactococcus cremoris*), Natto (*Bacillus subtilis* var. natto), Wine (*Leuconostoc oenos*), Sake (*Leuconostoc inesenteroides*), Polymyxin (*Bacillus polymyxa*), Colistin (*Bacillus colistrium*), Bacitracin (*Bacillus licheniformis*), L-Glutamic acid (*Brevibacterium lactofermentum*, *Microbacterium ammoniaphilum*), and acetone and butanol (*Colstridium acetobutylicum*, Clostridiumsaccharoperbutylacetoni-cum). See generally M. Sanders, Bacteriophages of Industrial Importance, in PHAGE ECOLOGY, 211–44 (S. Goyal, C. Berba and G. Bitton eds. 1987). *Escherichia coli* genetically engineered to produce materials such as chymosin, insulin, or Factor VIII by fermentation is susceptible to phage infection. Thus, the present invention may, for example, be employed in a fermentation process for producing any of the foregoing products with the foregoing bacteria in the manner described herein.

Starter cultures employed in practicing the present invention may be in any physical form, including liquid cultures of the fermentation bacteria in a suitable growth medium, as well as lyophilized cultures and frozen cultures prepared therefrom.

Starter cultures employed in the present invention are preferably defined cultures, that is, cultures of known bacterial content. Such defined cultures may be either single strain cultures, i.e., pure cultures, or multiple strain cultures, i.e., mixed cultures. All of the bacteria in the culture may contain the defense mechanism described herein, or some of the bacteria may contain the defense mechanism while others do not.

The fermentation apparatus and conditions under which fermentation may be selected and determined by persons of skilled in the art to produce the desired product, in accordance with known fermentation techniques. Bacteria of the present invention may be employed with or without rotation with other bacteria in a rotation strategy. When employed in a rotation strategy, the other, or second, bacteria employed may be nonisogenic or isogenic (i.e., have the same bacteriophage binding characteristics) with the bacteria of the present invention. Where isogenic bacteria are employed as the second bacteria in the rotation strategy, they may carry a different bacteriophage defense mechanism (including, but not limited to, any of those defense mechanisms set forth below)

D. ADDITIONAL DEFENSE MECHANISMS

As will be appreciated by those skilled in the art, bacteria of the present invention may optionally include one or more additional bacteriophage defense mechanisms in addition to the phage-inducible suicide system described herein. The additional bacteriophage defense mechanism(s) may be directed against the same or different bacteriophage as the phage-inducible suicide system described herein. Any additional bacteriophage defense mechanism may be employed, including, but not limited to, restriction/modification (R/M) systems and abortive infection (Abi) systems including phage-encoded resistance (PER) systems (as described in U.S. Pat. No. 5,538,864 to C. Hill and T. Klaenhammer), and the particular plasmid-based defense mechanisms as described in U.S. Pat. No. 4,883,756, 4,931,396; 4,732,859; 4,918,014; and 4,874,616 (applicant specifically intends that the disclosures of all U.S. Patent references cited herein be incorporated herein by reference. Abortive infection systems are particularly preferred.

E. DISCUSSION

Described herein is a novel bacteriophage protection strategy by genetic engineering of a mechanism that aborts the phage infection and intentionally kills the propagation host. As described below, the killing capacity of a three gene restriction cassette extracted from the LlaI R/M operon was exploited to develop a novel bacterial suicide system, triggered by a phage infection. The phage ϕ31-inducible promoter used to drive expression of the LlaIR+ cassette did not exert detrimental effects on the host in the absence of a phage infection. However, when transcription of the restriction cassette was initiated by phage infection, the plaquing efficiencies of ϕ31 and related phages were limited to very low levels of $10^{-4}$–$10^{-6}$. Moreover, phage progeny that escape restriction are not modified and will continue to suffer full restriction in subsequent attempts to infect host cells carrying ϕ31P/LlaIR+. As a result, any phage development within liquid cultures is severely retarded since each new host infected is triggered to commit suicide and destroy the incoming phage genome.

Both components of this particular embodiment of a bacterial suicide system, the category of death gene and the inducible expression signal, are unique. First, the promoter and restriction cassette are of lactococcal origin and, therefore, could be considered within a Generally Recognized As Safe (GRAS) category for food-grade applications. The GRAS status of this phage protection system allows deployment of the ϕ31P/LlaIR+cassette in starter cultures used in dairy fermentations. Second, to our knowledge, this is the first attempt to employ a restriction endonuclease component of an R/M system as a death gene in a conditional-suicide system. Numerous types of conditional-suicide systems have been developed where potent killing genes are coupled to inducible expression signals (reviewed by S. Molin et al., Annu. Rev. Microbiol. 47:139–166 (1993)). The combinations are designed not to interfere with normal growth and expression occurs under very specific conditions defined by the physical or chemical composition of the environment. Environmental signals used to trigger expression of bacterial suicide systems have included IPTG (A. Bej et al., *Appl. Environ. Microbiol.* 54: 2472–2477 (1988); K. Knudsen et al., *Appl. Environ. Microbiol.* 61:985–991 (1995); D. Kloos et al., *J. Bacteriol.* 176:7352–7361 (1994)), poor nutrient conditions (K. Tedin et al., *J. Biotechnol.* 39:2 137–148 (1995)), limitation of phosphate (T. Schweder et al., *Appl. Microbiol. Biotechnol.* 42:718–723 (1995)) or tryptophan (S. Molin et al., *Bio/Technol.* 5:1315–1318 (1987)), and availability of aromatic compounds in environment (A. Contreras et al., *Appl. Environ. Microbiol.* 57:1504–1508 (1991)). Conditional suicide systems in bacteria have been developed for a single purpose, to prevent release of recombinant strains outside a controlled environment. Signals most successfully applied are those directing plasmid transfer (Gerdes et al., *New Biologist* 2:946–956 (1990); E. Bahassi et al., *Mol. Microbiol.* 15(6):1031–1037 (1995); R. Roberts et al., *J. Mol. Biol.* 237:35–51 (1994); S. Tsuchimoto et al., *Mol. Gen. Genet.* 215:463–468 (1989)). The death genes studied most extensively in these applications are two-component toxin/antidote *E. coli* suicide systems involved in postsegregational killing of plasmid-free cells. Suicide systems of this kind include members of the gef gene family, such as hok/sok gene pair responsible for the maintenance of plasmid Rl (S. Molin et al., supra (1987); K. Gerdes et al., supra (1990)) and hok/sok homologous chromosomal loci relF (K. Gerdes et al., supra (1986); K. Knudsen et al., *Appl. Environ. Microbiol.* 61:985–991 (1995)) and gef (L. Poulsen et al., Mol. Microbiol. 5:1639–1648 (1991)), ccd loci of sex-factor F (E. Bahassi et al., supra (1995)), parDE of RP4 plasmid (R. Roberts et al., supra (1994)), and pem of R100 (S. Tsuchimoto et al., supra (1989)). Potent killing genes used to design several suicide systems have also included the following: gene E from ϕ174 (D. Kloos et al., supra (1994)), phage ϕT7 lysozyme gene (T. Schweder et al., supra (1995)), gene S from ϕλ (K. Tedin et al., supra (1995)), *Bacillus subtilis* sacb gene (G. Recorbet et al., *Appl. Environ. Micro-* biol. 59:1361–1366 (1993)), barnase from *Bacillus amyloliquefaciens* (G. Strittmatter et al., *Bio/Tech.* 13:1085–1089 (1995)), and endonucleases from *Serratia marcescens* (T. Ball et al., Gene, 57:183–192 (1987)) and *Staphylococcus aureus* (A. Davis et al., *J. Biol. Chem.* 18:6544–6553 (1977)). In contrast to these suicide systems, the φ31P/LlaIR+ cassette is designed to provide protection against bacteriophage by creating a genetic trap that triggers after a phage infection and destroys both the phage genome and bacterial host.

The efficiency of the φ31P/LlaIR+ system was improved by two approaches. Presenting the suicide cassette on a high-copy-number replicon dramatically increased the level of phage restriction. This construction was largely responsible for development of a functionally effective defense system. Noting this, efforts to stabilize the phage-inducible restriction cassette in the chromosome would likely require use of a stronger promoter, a promoter recognized earlier in the phage development cycle, and/or a more effective death gene. Second, the presence of C. LlaI elevated restriction 10-fold against phage φ31. This regulatory protein appears to serve a bifunctional role in the native LlaI R/M operon by both repressing transcription and promoting restriction activity (D. O'Sullivan and T. Klaenhammer, Vol. 85, p.591–595. In J. J. Feretti, M. S. Gilmore, T. R. Klaenhammer, F. Brown (eds.), Genetics of the Streptococci, Enterococci, and Lactococci. Dev. Biol. Stand. Basel, Karger. 1995)). In this latter role, the C -LlaI protein has been proposed to enhance RNA stability and facilitate translation of the three gene restriction cassette. The existing φ31P/LlaIR+ system could be improved by incorporating llaIC within the cassette.

The φ31P trigger promoter selected and used in the design of the suicide system presents two inherent limitations, timing and tight recognition specificity. φ31P is a middle phage promoter that is transcribed approximately 20 minutes following the phage infection (S. Walker et al., *J. Dairy Sci.* 78: 108 (1995)). Considering the dynamics of the phage life cycle, activation of the φ31P/LlaIR+ cassette at this later stage does allow some DNA to escape restriction and progeny phage to survive in 15% of the infected cells. The efficiency of the LlaI-based suicide system could be improved substantially if the restriction cassette is expressed from a phage-specific promoter triggered earlier during the phage infection. However, it is critical that the earlier trigger promoter is completely phage-specific and that it is not recognized by bacterial host in the absence of phage. Such trigger promoter is being sought, but has not yet been defined. Therefore, in the design of the phage-induced suicide system a fine balance must be accomplished between tight control of expression signals and the optimal stage of temporal phage development when those promoters are recognized. Suicide genes expressed too late in the cycle may serve only to facilitate cell death and release of assembled phage progeny. Second, because of the high specificity of phage expression signals, the φ31P/LlaIR+ based suicide cassette can be triggered only by phage φ31 or related phages that contain similar promoter regions or encode transcriptional factors with similar promoter specificity. Attempts to induce the φ31P promoter with other phages from the P335 species, as well as phages from other lactococcal species (P936 and c2) were not successful (data not shown). Due to this promoter specificity, the defense system would not be practically effective against the diverse combinations of phage strains and species that attack lactococci.

In conclusion, disclosed is a novel bacteriophage defense strategy that programs cell death and intracellular destruction of phage DNA post infection. The system is designed as a genetic trap to invite phage adsorption and DNA injection. In bacterial populations where every cell harbors a phage-inducible suicide cassette, infected cells hydrolyze the phage genome and undergo programmed cell death in an altruistic fashion designed after naturally-occurring abortive infection mechanisms. Various combinations of death genes and promoter elements can be envisioned to design similar systems for virtually any bacteria. When alone, or combined with other defense systems, phage-triggered, intracellular suicide/defense systems are capable of trapping and eliminating phages, and their genetic potential, from fermentation environments.

The examples which follow are illustrative of specific embodiments of the invention, and various uses thereof. They are set forth for explanatory purposes only, and are not to be taken as limiting the invention.

EXAMPLE 1

Bacteria, bacteriophage, and plasmids

*Escherichia coli* MC1061 (N. Casadaban and S. Cohen, *J. Mol. Biol.* 138:179–210 (1980)) was used as primary transformation host throughout the study. *E. coli* MC1061 derivatives harboring plasmids pTRK414L or pTRK414H were designated NCK785 and NCK781, respectively. *Lactococcus lactis* NCK690 was the sensitive host for bacteriophage φ31. This strain is a derivative of *L. lactis* NCK203 (C. Hill et al., *Appl. Environ. Microbiol.* 55:2416–2419 (1989)) spontaneously cured of all plasmids, except a 7.5 kb plasmid (E. Durmaz, unpublished data). *L. lactis* NCK690 harboring pTRK414L or pTRK414H were designated NCK786 and NCK782, respectively. Phage φ31 is a small isometric, P335 species, cohesive ended, lactococcal bacteriophage with a double-stranded DNA genome of 31.9 kb. This phage is sensitive to both AbiA-mediated abortive resistance and LlaI restriction (T. Alatossava and T. Klaenhammer, *Appl. Environ. Microbiol.* 57:1346–1353 (1991)). Recombinant phages φ31.1, 031.2, φ31.7, and φ31.8 are Per31-resistant derivatives of phage φ31 (D. O'Sullivan et al., *Appl. Environ. Microbiol.* 59:2449–2456 (1993)), selected following a homologous recombination event between the phage genome and L. lactis NCK203 chromosome (D. O'Sullivan and T. Klaenhammer, in Abstracts of the 7th International Symposium on the Genetics of Industrial Microorganisms, Montreal, Canada, p.186 (1994); E. Durmaz et al., *J. Dairy. Sci.* 78:109 (1995)). Plasmids used or constructed in this study are listed in Table 1.

EXAMPLE 2

Culture conditions and bacteriophage assays

*E. coli* strains were grown at 37° C. in Luria-Bertani (LB) medium (J. Sambrook et al., Molecular cloning: a laboratory manual, 2nd ed. Cold Spring Harbor Laboratory, Cold Spring Harbor, N.Y. (1989)) or brain heart infusion medium (BHI, Difco Laboratories, Detroit, Mich.). Erythromycin (Em) 100 µg/ml was added for selective propagation of *E. coli* in broth where appropriate. Agar plates (1.5% granulated agar, BBL Microbiology systems, Cockeysville, Md.) were prepared from BHI medium. Erythromycin (Em$^r$) resistant *E. coli* transformants were selected on BHI agar with 200 µg/ml erythromycin. *L. lactis* was propagated at 30° C. in M17 broth (Difco) containing 0.5% glucose (GM17). Erythromycin 2.5 µg/ml or chloramphenicol 3.0 µg/ml were used for antibiotic selection in lactococci.

Bacteriophage plaque assays were conducted as described previously (B. Terzaghi and W. Sandine, Appl. Microbiol. 29:807–813 (1975)). Center of infection (COI) assays, one-step growth curves, and burst size determinations were all performed at 30° C. in accordance with known techniques (W. Sing and T. Klaenhammer, J. Gen. Microbiol. 136:1807–1815 (1990)).

TABLE 1

Plasmids Used or Constructed Herein.

| Plasmid | Relevant Characteristics |
| --- | --- |
| pBluescript KS II+ | 2.96 kb, Ap$^r$ (Stratagene) |
| pTRKL2 | 6.4 kb, lacZ, Em$^r$ |
| pTRKH2 | 6.9 kb, lacZ, Em$^r$ |
| pTRK370 | 15.9 kb, encodes complete llaI operon, Em$^r$, R$^+$/M$^+$ |
| pTRK394 | 6.6 kb, Ap$^r$, pBluescriptIIKS+ with 3.7 kb PvuII-ClaI DNA fragment from pTRK370 that contains the promoterless llaI.1, llaI.2, llaI.3 cassette. |
| pTRK395 | 9.8 kb, Em$^r$, pTRK12 with 3.7 kb PvuI-HindIII DNA fragment from pTRK394 that contains the promoterless llaI.1, llaI.2, llaI.3 cassette. |
| pTRK397 | 10.3 kb, Em$^r$, pTRK12 with 3.7 kb PvuI-XhoI DNA fragment from pTRK394 that contains the promoterless llaI.1, llaI.2, llaI.3 cassette. |
| pTRK414L | 10.1 kb, Em$^r$, the 239 bp FspI-BamHI $\phi$31 promoter fragment from pTRK391[4] added to pTRK395 |
| pTRK414H | 10.6 kb, Em$^r$, the 239 bp FspI-BamHI $\phi$31 promoter fragment from pTRK391[4] added to pTRK397 |
| pTRK400 | 7.9 kb, Km$^r$, Cm$^r$, pNZ18 with 2.4 kb fragment from pTRK370, encoding llaIC with the native promoter from the llaI operon |

[1] D. O'Sullivan and T. Klaenhammer, Gene 137:227–231 (1993).
[2] D. O'Sullivan et al., J. Bacteriol. 177:134–143 (1995).
[3] G. Djordjevic and T. Klaenhammer, Plasmid 35, 37–45 (1996).
[4] D. O'Sullivan et al., Bio/Technology 14:82–87 (1996).

EXAMPLE 3

Plasmid and phase DNA isolation and molecular cloning

Rapid isolation of E. coli plasmid DNA was accomplished by an alkaline lysis method of H. Birnboim and J. Doly, Nucleic Acids Res. 7: 1513–1519 (1979). Large scale isolation of E. coli plasmid DNA was accomplished using the QIAGEN plasmid kit (QIAGEN, Inc., Chatsworth, Calif.) following the manufacturer's instructions. Isolation of plasmid DNA from lactococci was performed by the alkaline lysis protocol described by B. Bojovic et al., Appl. Environ. Microbiol. 57:385–388 (1991). Phage DNA was isolated using the large scale protocol described by R. Raya et al., Appl. Environ. Microbiol. 55:2206–2213 (1989). Standard techniques were used for endonuclease restriction, dephosphorylation and ligation of bacterial DNA (Sambrook et al., supra (1989)). Ligation of phage DNA was performed as described by Sambrook et al., supra (1989) with the following modifications: phage DNA fragments were heated at 65° C. for 15 minutes before adding vector DNA; the ligation mixture was heated at 65° C. for an additional 10 minutes, and then slowly cooled to 30° C. before adding ligation buffer and T4 DNA ligase. All DNA used in cloning reactions was first purified in SeaKem GTG agarose (FMC BioProducts, Rockland, Maine) and extracted using QIAEX DNA extraction kit (QIAGEN, Inc., Chatsworth, Calif.) following the manufacturer's instructions.

EXAMPLE 4

Bacterial transformation

Electrocompetent E. coli cells were prepared as described by W. Dower et al., Nucleic Acids Res. 16:6127–6145 (1988) and electroporated using the Gene Pulser™ apparatus (Bio-Rad Laboratories, Richmond, Calif.). L. lactis cells were electrotransformed as described by G. Djordjevic and T. Klaenhammer, Plasmid 35:37–45(1996)

EXAMPLE 5

Construction of the $\phi$31P/LlaIR+ cassette

Figure 1B:
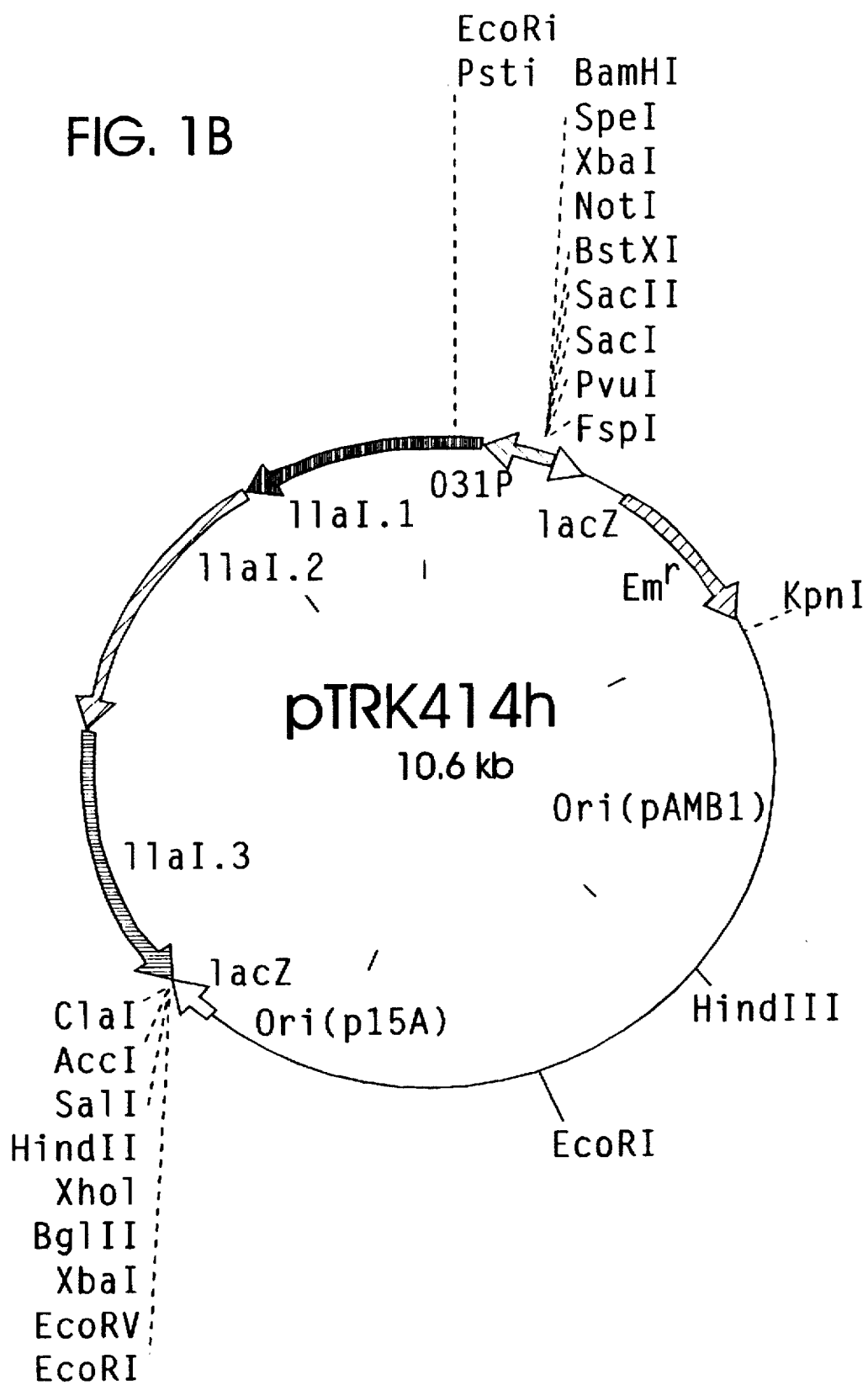
Figure 2B:
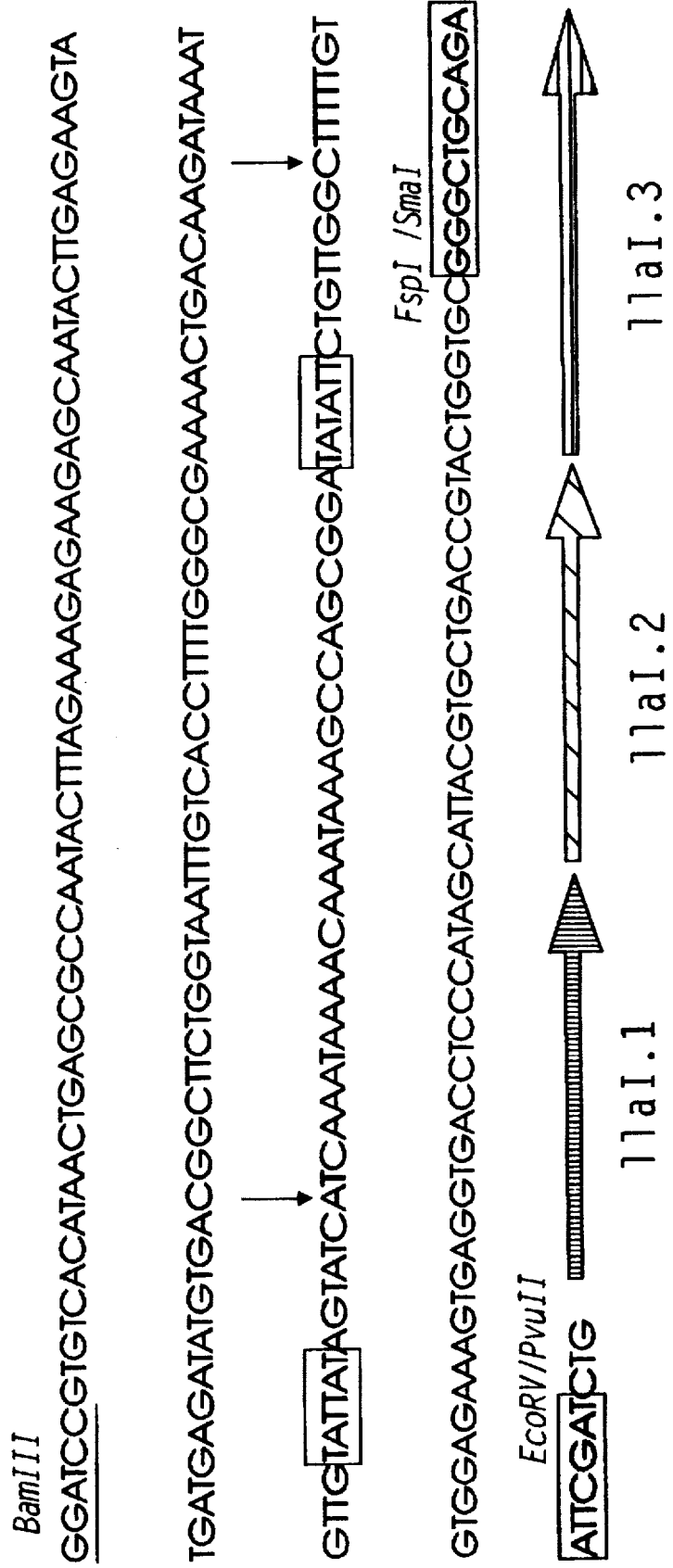
FIG. 2B shows the nucleotide sequence of the phage-inducible promoter, designated φ31P (SEQ ID NO:2), fused to the LlaR+ restriction cassette composed of three genes llaI.1, llaI.2, and llaI.3. The transcription start sites at nucleotides 703 and 744 are represented by vertical arrows. The −10 consensus promoter regions are boxed. The shaded region represents a portion of the multiple coning sites (MCS) from pBluescript KS⁺. Junctions between the MCS and φ31P and llaI.1 are represented by FspI/SmaI and EcoRV/PvuII, respectively. The BamHI site was introduced by the oligonucleotide primer used for PCR subcloning of the φ31P.

The promoterless LlaI restriction cassette, composed of three genes llaI.1, llaI.2, and llaI.3, designated LlaIR+, was first cloned as a 3.7-kb PvuII-ClaI fragment from the R/M plasmid pTRK370 into pBluescript II KS+ (pTRK394, Table 1). The LlaIR+cassette was then subcloned into the low and high-copy-number shuttle vectors pTRKL2 and pTRKH2 to generate pTRK395 and pTRK397, respectively (see Table 1). To prevent transcription from lacZ promoter, the restriction cassette was positioned in an orientation opposite to lacZ in all three plasmids. The 239 bp FspI-BamHI DNA subfragment encoding a phage-inducible promoter with tandem transcription starts was isolated from pTRK391 (D. O'Sullivan et al., Bio/Technol. 14:82–87 (1996)) and designated $\phi$31P. The promoter element exhibits no detectable activity in the absence of a $\phi$31 infection (S. Walker et al., supra 1995). The $\phi$31P fragment was cloned 5' of the LlaIR+ cassette encoded on pTRK395 and pTRK397, and pTRK414L (low copy number) and pTRK414H (high copy number) plasmids were recovered in E. coli MC1061 (see Table 1, FIG. 1, and FIG. 2.). The two plasmids were transformed subsequently into L. lactis NCK690 by electroporation. No differences in transformation frequencies were observed when E. coli or L. lactis were transformed with pTRK414L and pTRK414H, compared to pTRK395 and pTRK397 encoding the promoterless LlaIR+cassette. As LlaI (R$^+$/M$^-$) plasmids are lethal in L. lactis (D. O'Sullivan et al., J. Bacteriol. 177:134–143 (1995)), it was evident that the $\phi$31P promoter was not recognized in these L. lactis transformants in the absence of a phage infection. The plasmids were stable during repeated subculture under antibiotic selection.

EXAMPLE 6

Functional characterization of the $\phi$31P/LlaIR+ cassette

Standard plaque assays were used to evaluate the efficiency at which phage $\phi$31 infected L. lactis harboring the restriction cassettes (Table 2). When L. lactis NCK690 contained either pTRK395 or pTRK397, both encoding the promoterless restriction cassette, was infected with phage $\phi$31 it plaqued at full efficiency. However, in the presence of pTRK414L that contains the $\phi$31P/LlaIR+cassette on a low-copy number replicon, the EOP was reduced to 0.5 with no notable changes in plaque size or morphology. In the presence of pTRK414H that contains the $\phi$31P/LlaIR$^+$on the high-copy number replicon pTRK414H, the EOP for $\phi$31 was reduced dramatically to $2.2 \times 10^{-4}$ (Table 2) and the plaques were very small and aberrant in size. Therefore, the $\phi$31P/LlaIR+ cassette did restrict the plaquing efficiency of phage $\phi$31 at levels that correlated with the high or low copy number of the replicon on which it was cloned.

Figure 3A:
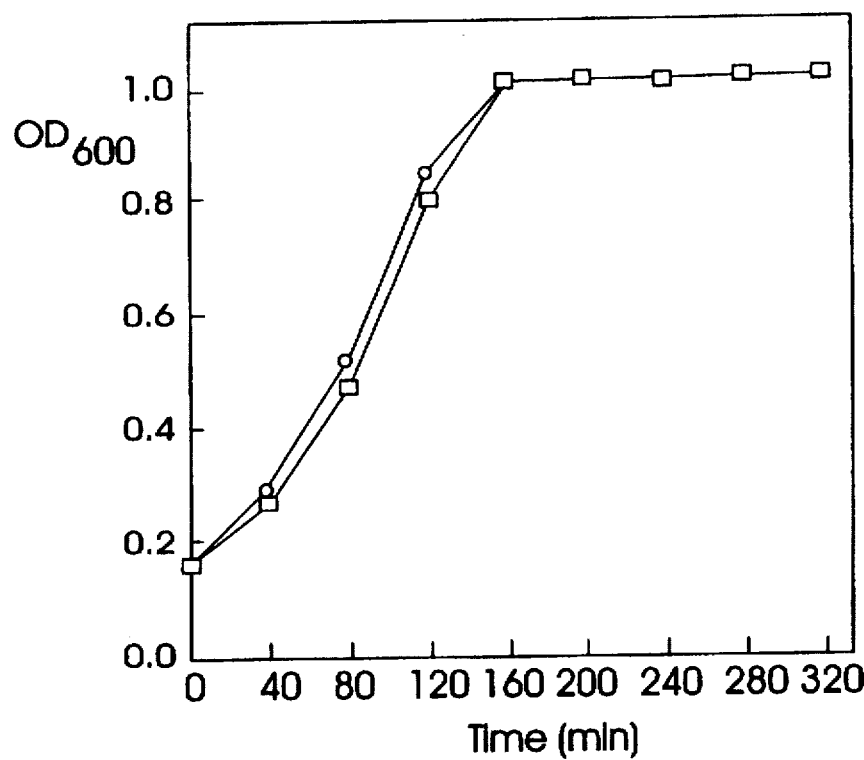
FIGS. 3A to 3B show the effect of phage φ31 on the growth of *L. lactis* NCK690 and *L. lactis* NCK690 (pTRK414H).
Figure 3B:
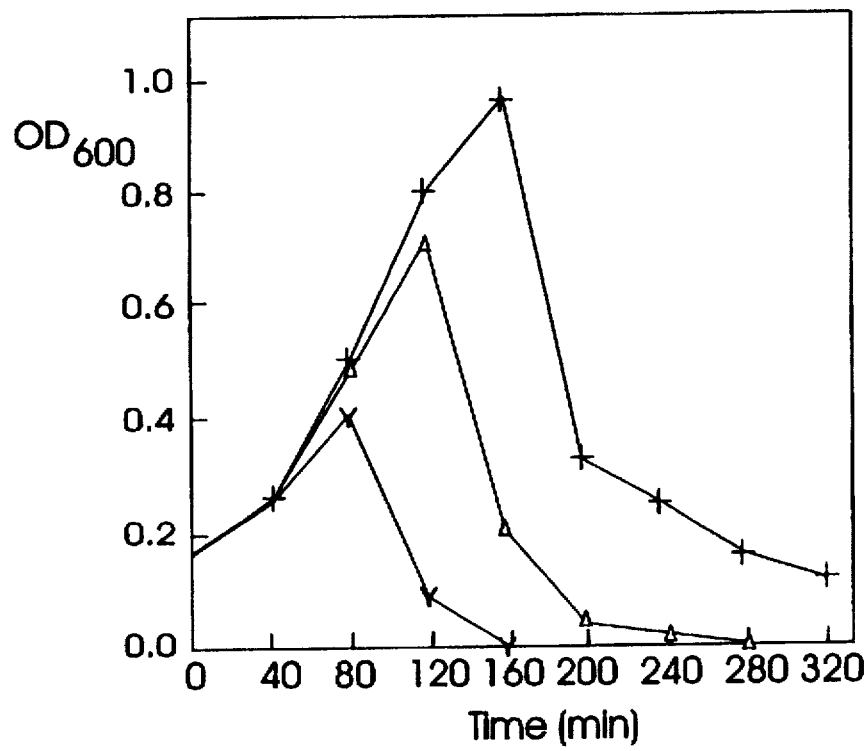
Figure 3C:
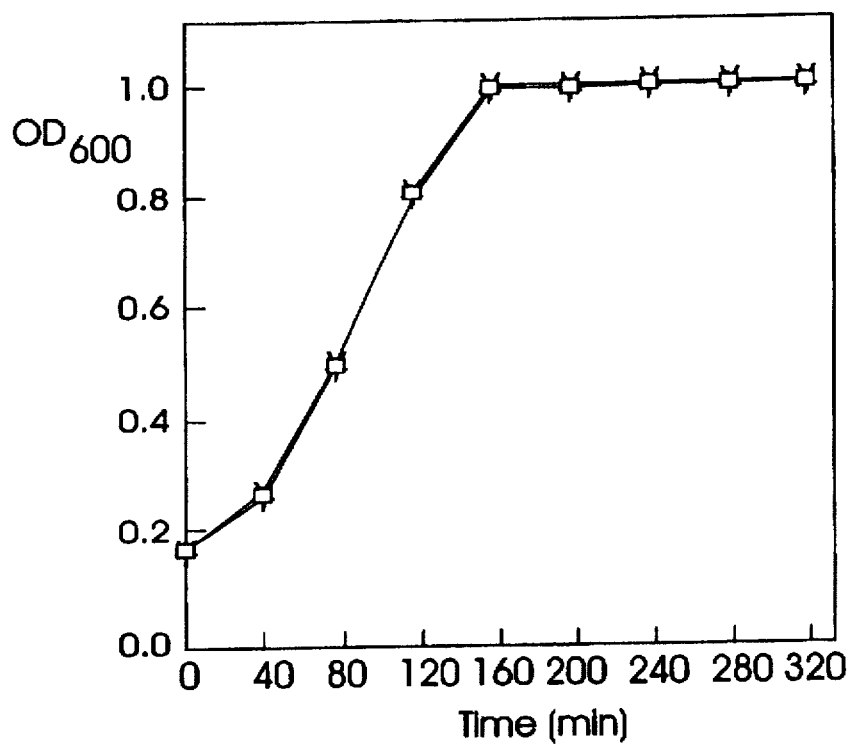
FIG. 3C shows growth curves of *L. lactis* NCK690 (pTRK414H) infected with 10⁷ (open triangle with apex down), 10⁶ (open triangle with apex up), and 10⁵ (open diamond) pfu/ml of phage φ31.

L. lactis NCK690 and NCK690 (pTRK414H) were also challenged with $10^5$, $10^6$, and $10^7$ pfu/ml of phage $\phi$31 in broth cultures (FIG. 3). The multiplicities of infection (MOI) ranged from 0.001 to 0.1. As expected, phage $\phi$31 readily lysed L. lactis NCK690 (FIG. 3B). In contrast, lactococcal cells harboring the suicide system on pTRK414H did not suffer phage-induced cell lysis at any level of infection and continued to grow normally (FIG. 3C). When the suicide system was presented on the low copy replicon, pTRK414L, phage φ31 was still able to lyse the culture when challenged with $10^5$–$10^7$ pfu/ml. These results correlated with negligible effect of pTRK414L on the EOP of phage φ31 in L. lactis NCK690 (Table 2).

TABLE 2

Efficiency of plaquing (EOP) for phage φ31 on *Lactococcus lactis* NCK690 harboring phage-inducible LlaI restriction cassette.

| Plasmid Content | Relevant Characteristics | EOP |
|---|---|---|
| None* | Propagation host for phage φ31 | 1.0 |
| pTRK395 | Promoterless LlaIR+ cassette encoded on the low-copy plasmid | 1.0 |
| pTRK397 | Promoterless LlaIR+ cassette encoded on the high-copy plasmid | 1.0 |
| pTRK414L | The φ31P/LlaIR+ cassette encoded on the low-copy plasmid | 0.5 |
| pTRK414H | The φ31P/LlaIR+ cassette encoded on the high-copy plasmid | $2.2 \times 10^{-4}$ |
| pTRK400 | The regulatory protein C.LlaI encoded on a high-copy plasmid | 1.0 |
| pTRK414L + pTRK400 | The φ31P/LlaIR+ cassette encoded on the low-copy plasmid in the presence of the regulatory protein C.LlaI | 0.6 |
| pTRK414H + pTRK400 | The φ31P/LlaIR+ cassette encoded on the high-copy plasmid in the presence of the regulatory protein C-LlaI | $2.0 \times 10^{-5}$ |

*L. lactis NCK690 is a derivative of L. lactis NCK203 cured of all plasmids, but one (E. Durmaz, unpublished data).

EXAMPLE 7

Evaluation of the efficiency of the φ31P/LlaIR+ restriction cassette

Figure 4:
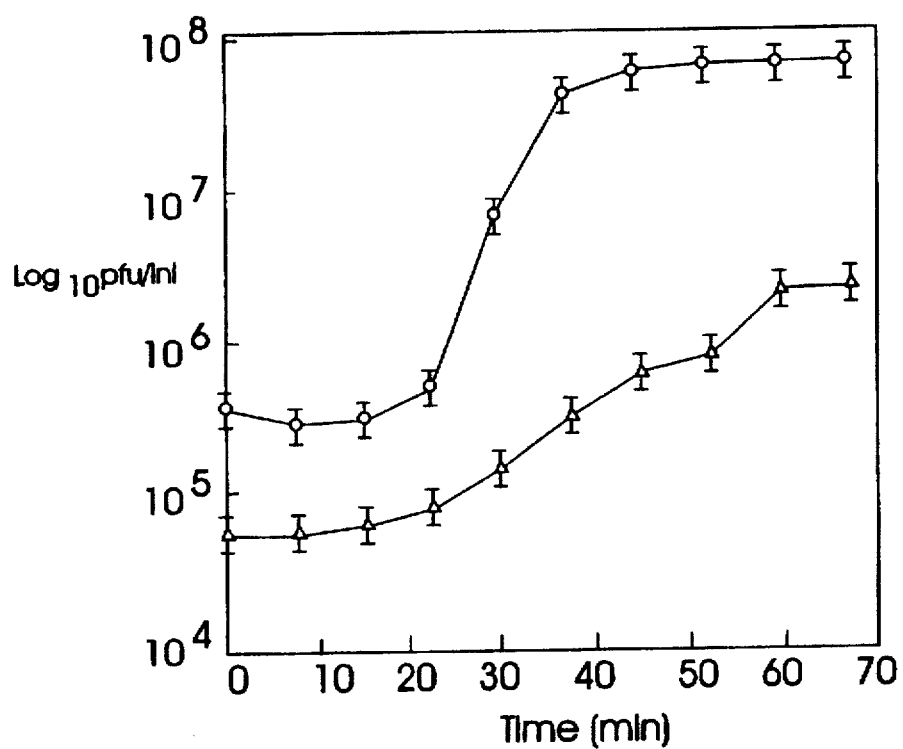
FIG. 4 shows one-step growth curves for phage φφ31 infection of *L. lactis* NCK690 (filled circle) and *L. lactis* NCK690(pTRK414H) (filled triangle).

One-step growth curves and center of infection (COI) assays for phage φ31 were conducted on L. lactis NCK690 (pTRK414H) harboring the φ31P/LlaIR+ suicide cassette (FIG. 4). Cells were propagated until the $OD_{600}$ reached 0.4 and then infected with $10^8$ pfu/ml of phage φ31 (MOI=5). The number of infective centers (pfu/ml) formed initially on L. lactis NCK690 (pTRK414H) was $5.4 \times 10^4$, 85% lower than on L. lactis NCK690 ($3.6 \times 10^5$; FIG. 4). Only 15% of infected cells harboring (pTRK414H) released progeny phages and phage development was notably retarded over the course of the one-step growth experiment. Phage burst sizes in L. lactis NCK690, with and without pTRK414H, were estimated at 41 and 161, respectively. Therefore, the φ31P/LlaIR+ suicide cassette encoded on pTRK414H reduced the burst size of phage φ31 four-fold and severely limited the efficiency at which infections were completed.

Phages present in plaques formed on lawns of the restrictive host L. lactis NCK690 (pTRK414H) were evaluated for their sensitivity or resistance to restriction by the LlaI R/M system. Several small plaques were recovered from L. lactis NCK690 (pTRK414H) and suspended by vortexing in 2 ml GM17. The samples were then plaqued on L. lactis NCK690 (R⁻/M⁻), L. lactis NCK690 (pTRK370) (R⁺/M⁺), and on L. lactis NCK690 (pTRK414H). Approximately $10^7$ pfu/ml were obtained on L. lactis NCK690. No plaques were detected on L. lactis NCK690 bearing either pTRK370 or pTRK414H. Therefore, progeny phages released from cells bearing pTRK414H remained fully sensitive to restriction by LlaI. These results are consistent with the appearance of small aberrant φ31 plaques on L. lactis NCK690 (pTRK414H). Phage φ31 is limited in burst size and progeny phage continue to be severely restricted during subsequent infections of surrounding cells in the lawn.

EXAMPLE 8

C.LlaI enhances the φ31P/LlaIR+ suicide system

The llaIC gene product, encoded upstream of the methylase llaIM gene in the llaI R/M operon, enhances the restriction activity of the LlaI system (D. O'Sullivan and T. Klaenhammer, supra (1995); G. Djordjevic and T. Klaenhammer, supra (1996)). The effects of C-LlaI on the efficiency of the phage-inducible restriction cassette were evaluated. Plasmid pTRK400 encoding llaIC (Table 1) was introduced into L. lactis NCK690, L. lactis NCK690 (pTRK414L), and L. lactis NCK690 (pTRK414H). The pTRK400 transformants were challenged with $10^6$ pfu/ml of phage 31 (MOI of 0.01). The results in Table 2 show that the EOP for φ31 on L. lactis NCK690 (pTRK414H+pTRK400) was $2.0 \times 10^{-5}$, ten-fold lower than the EOP of $2.2 \times 10^{-4}$ obtained for NCK690 bearing pTRK414H alone. No enhancement was observed due to the presence of llaIC in lactococcal cells harboring pTRK414L (Table 2). This likely reflects the low baseline level of restriction activity encoded on the low copy number vector. At functional levels of restriction activity, the C-LlaI protein markedly enhanced the effectiveness of the φ31P/LlaIR+ cassette.

EXAMPLE 9

Effect of the φ31P/LlaIR+restriction cassette against related phases

The phage-inducible promoter φ31P is positioned near the right cos end of the phage φ31 genome (D. O'Sullivan et al., supra (1996)). This region has been recently identified in the genomes of a series of φ31-derived, Per31 resistant, recombinant phages (E. Durmaz et al., supra (1995)). Therefore, we evaluated if the φ31P/LlaIR+suicide cassette would also confer resistance to φ31-derived recombinant phages (Table 3). In all cases, the recombinant phages were restricted by the presence of the φ31P/LlaIR+suicide cassette at levels which were at least 10-fold greater than phage φ31 (Table 3). Plaques formed by the recombinant phages were substantially smaller in size and their appearance altered as compared to φ31 plaques. The lower EOPs observed for Φ31-derived recombinant phages suggest that they are more sensitive to the lethal activity of the φ31P/LlaIR+ cassette than phage φ31. Of the φ31-derived recombinant phages, phage φ31.1 was the most sensitive to restriction by the φ31P/LlaIR+ suicide cassette.

TABLE 3

Efficiency of plaquing (EOP) for phage φ31 and φ31-derived recombinant phages on *Lactococcus lactis* NCK690 (pTRK414H)

| Phage | EOP* | Plaque size** on L. lactis NCK690 |
|---|---|---|
| φ31 | 1.0 | 2.1 |
|  |  | Plaque size on L. lactis NCK690 (pTRK414H) |
| φ31 | $2.14 \times 10^{-4}$ | 0.5–1.3 |
| φ31.1 | $5.24 \times 10^{-6}$ | 0.4 |
| φ31.2 | $1.86 \times 10^{-5}$ | 0.5–0.7 |
| φ31.7 | $3.04 \times 10^{-5}$ | 0.5–0.7 |
| φ31.8 | $3.67 \times 10^{-5}$ | 0.5–1.2 |

EOPs represent the average of 3–4 independent experiments.
**Plaque size (mm) on sensitive host L. lactis NCK690 ranged from 2.1 (φ31), 1.9 (φ31.8) 1.8 (φ31.1, φ31.2) to 1.7 (φ31.7).

Figure 5A:
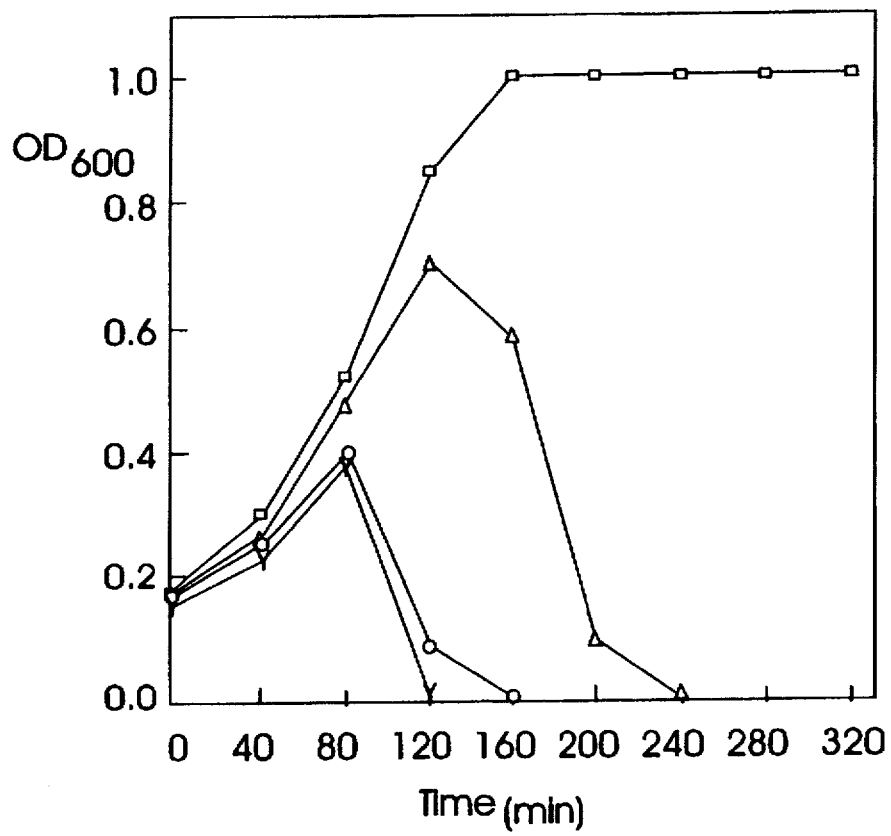
FIGS. 5A and 5B shows the effect of phage φ31-derived recombinant phages on growth of *L. lactis* NCK690 and *L. lactis* NCK690 (pTRK414H)
Figure 5B:
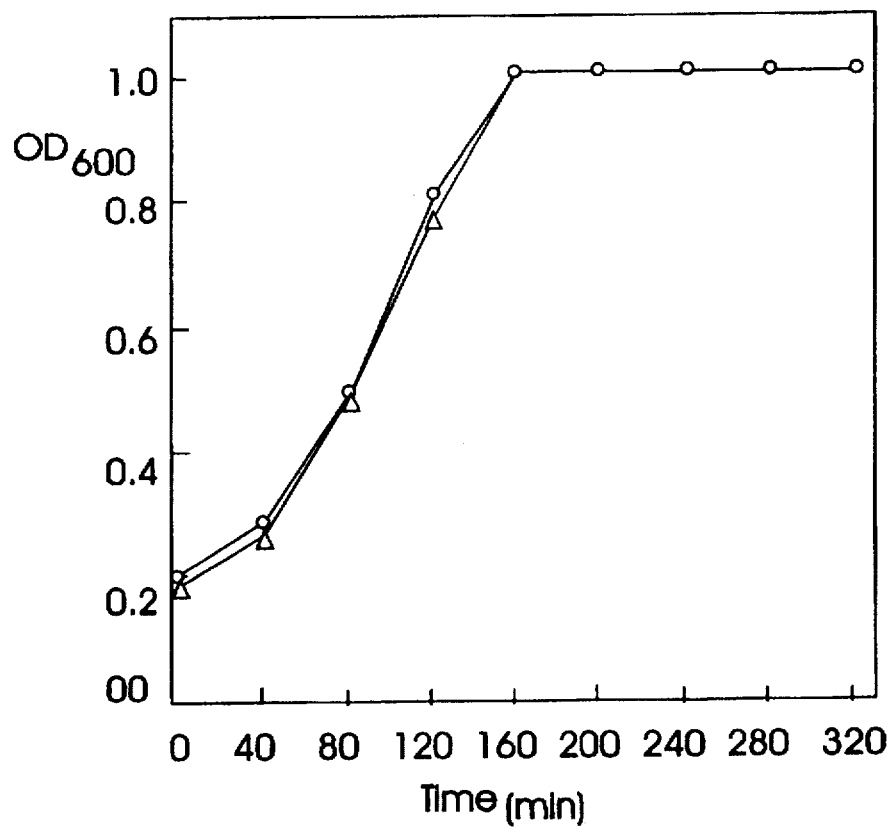

L. lactis NCK690 (pTRK414H) broth cultures were also challenged with φ31-derived recombinant phages. Four cultures at an $OD_{600}$ of 0.15–0.2 were individually infected with $10^7$ pfu/ml (MOI of 0.1) of the recombinant phages φ31.1 and φ31.8 and cell growth monitored over 320 min. (FIG. 5). Those cultures harboring pTRK414H were unaffected by the phage challenge and continued to grow normally.

EXAMPLE 10

Evaluation of the φ31P/LlaIR+ Cassette With Abortive Phage Defenses Per31 and AbiA In this Example, the llaIC gene and the φ31P/LlaIR$^+$ cassette were combined on the same replicon (pTRK414HT711aIC). The plasmid also contains the T7 terminator cloned 5' to the restriction cassette. When L. lactis NCK690 (pTRK414HT711aIC) was challenged with page φ31, the EOP was $4.4 \times 10^{-5}$ (Table 4), a five-fold lower compared to that on L. lactis NCK690 (pTRK414H).

The abortive phage defenses Per31 (D. O'Sullivan et al., Bio/Technology 14: 82–87 (1996)) are encoded on high-copy-number plasmids pTRK375 and pTRK406, respectively. pTRK375 is a pNZ-18-derivative (de Vos, (1987)) with a 4.5-kb fragment of φ encoding phage replication origin (E. Durmaz and T. Klaenhammer, Appl. Environ. Microbiol. 61: 1266–1273 (1995)). pTRK406 is also a pNZ18-derivative, with a 2.2-kb fragment encoding the abiA abortive infection gene (Dinsmore and Klaenhammer, 1996). To evaluate the efficiency of the φ31P/LlaIR+ cassette in L. lactis in the presence of Per31 or AbiA, plasmid pTRK414HT711aIC was combined with pTRK375 and pTRK406, respectively. When either Per31 or AbiA were present in trans, the EOP for phage φ31 was lowered to $<10^{-10}$ (Table 4). Similarly, when L. lactis NCK690 (pTRK414HT711aIC–pTRK375) and L. lactis NCK690 (pTRK414HT711aIC+pTRK406) broth cultures were challenged with $10^6$ pfu/ml (MOI=0.01) of φ31, phage was eliminated from the infected population which continued to grow normally.

TABLE 4

Efficiency of plaquing (EOP) of φ31PLlaIR$^+$ Cassette in Combination with Abortive Phage Defenses Per 31 and AbiA.

| Plasmid Content | Relevant Characteristics | EOP |
|---|---|---|
| pTRK414HT7llaIC | The φ31P/LlaIR$^+$ cassette and regulatory protein C.LlaI encoded on the same high-copy plasmid | $4.4 \times 10^{-5}$ |
| pTRK414HT7llaIC +Per31 | The φ31P/LlaIR$^+$ cassette and regulatory protein C.LlaI encoded on the same high-copy plasmid, in the presence of Per31 | $<10^{-10}$ |
| pTRK414HT7llaIC +AbiA | The φ31P/LlaIR$^+$ cassette and regulatory protein C.LlaI encoded on the same high-copy plasmid, in the presence of AbiA | $<10^{-10}$ |

The foregoing examples are illustrative of the present invention, and are not to be construed as limiting thereof. The invention is defined by the following claims, with equivalents of the claims to be included therein. a1

---

That which is claimed is:

1. A bacterial cell containing a recombinant bacteriophage defense mechanism, said defense mechanism comprising a bacteriophage promoter operatively associated with a heterologous DNA encoding a product lethal to said bacterial cell, wherein said bacterial cell is susceptible to infection by a bacteriophage, and wherein said promoter is activated upon the infection of said bacterial cell by said bacteriophage.

2. A bacterial cell according to claim 1, wherein said bacterial cell is a gram negative bacterial cell.

3. A bacterial cell according to claim 1, wherein said bacterial cell is an *Escherichia coli* bacterial cell.

4. A bacterial cell according to claim 1, wherein said bacterial cell is a gram positive bacterial cell.

5. A bacterial cell according to claim 1, wherein said bacterial cell is a Lactococcus bacterial cell.

6. A bacterial cell according to claim 1, wherein said recombinant defense mechanism is carried by an extrachromosomal plasmid.

7. A bacterial cell according to claim 1, wherein said heterologous DNA encodes an enzyme that degrades nucleic acid.

8. A bacterial cell according to claim 1, wherein:
said bacteriophage promoter is a phage φ31 promoter;
said heterologous DNA comprises the LlaI restriction cassette; and
said bacterial cell is a Lactococcus lactis bacterial cell.

9. A bacterial cell according to claim 1, wherein:
said bacteriophage promoter is a T7 promoter;
said heterologous DNA encodes barnase; and
said bacterial cell is an *Escherichia coli* bacterial cell.

10. A fermentation starter culture comprising a plurality of bacterial cells containing a recombinant bacteriophage defense mechanism, said defense mechanism comprising a bacteriophage promoter operatively associated with a heterologous DNA encoding a product lethal to said bacterial cell, wherein said bacterial cell is susceptible to infection by a bacteriophage, and wherein said promoter is activated upon the infection of said bacterial cell by said bacteriophage.

11. A starter culture according to claim 10, wherein said culture is a defined culture.

12. A starter culture according to claim 10, wherein said culture is a pure culture.

13. A starter culture according to claim 10, wherein said culture is useful for fermenting food.

14. A starter culture according to claim 10, wherein said culture is useful for fermenting milk.

15. A starter culture according to claim 10, wherein said bacterial cells are gram negative bacterial cells.

16. A starter culture according to claim 10, wherein said bacterial cells are *Escherichia coli* bacterial cells.

17. A starter culture according to claim 10, wherein said bacterial cells are gram positive bacterial cells.

18. A starter culture according to claim 10, wherein said bacterial cells are Lactococcus bacterial cells.

19. A starter culture according to claim 10, wherein said recombinant defense mechanism is carried by an extrachromosomal plasmid.

20. A starter culture according to claim 1, wherein said heterologous DNA encodes an enzyme that degrades nucleic acid.

21. A method of fermenting a substrate to produce a product, said method comprising:
   combining a fermentation medium and bacteria according to claim 1; and then
   fermenting the fermentation medium with said bacteria to produce said product.

22. A recombinant DNA comprising a bacteriophage promoter operatively associated with a heterologous DNA encoding a product lethal to a bacterial cell, wherein said bacteriophage promoter is activated by infection of a bacteriophage.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 888 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
GATCCGATGT TTATAAACAA AATCCACTTA GCAGAGCATT TGTAAGGTTG GTTGGTATTC    60

CAGTTACAGA CAGAGATATT GAAGAACATT TTACAAAATA TGATGAATCT AAAGATGTAT   120

TAATGCCAGA TTAATAACAA AAAAAGCCCA CTGCAATGGG CTTTAAAAAC AGATTTCTTA   180

ACTACTATTA TATCATAAAT ATAAGGAGTT GAGACACTAT GAGTAGAAGA TATAACCTTA   240

CTGACAGCGA CTTGAAAGCT ATAGAGAAGA AGCTCTTTAT GTGTCAACGA ATTGACCACG   300

CTATTCAATA TCGCAAGTAT GAGTTAGAAG TTAAACAATC ACATGATAAT AATGTAGGTG   360

GTGGTAGGTC AAGTATAATC TCAAAGCCAG TAGAAGATAT GGTTATGAAA TGGGATGCTG   420

ACAGTAAACT CCAAAGTCTA TATGAGTTTA AGAACCGAAT CAATGAGTTA CAAGATTGGT   480

TTGGAGATGA TGAAGATATG CAATTGGTAT TCCACTACCG TTGGTTATCT GGTAAACGTT   540

ATACAGTACC AGAGATAGCT GATAAGTGTC ACATAACAGA GCGCCAATAC TTTAGAAAGA   600

GAAGAGCAAT ACTTGAGAAG TATGATGAGA TATGTGACGG CTTCTGGTAA TTTGTCACCT   660
```

| | | | | | |
|---|---|---|---|---|---|
| TTTGGGCGAA | AACTGACAAG | ATAAATGTTG | TATTATAGTA | TCATCAAATA | AAACAAATAA | 720
| AGCCAGCGGA | TATATTCTGT | TGGCTTTTTG | TGTGGAGAAA | GTGAGGTGAC | CTCCCATAGC | 780
| ATTACGTGCT | GACCGTACTG | GTGCGCATCG | TGTAGCCTTT | GATAAGAATA | GAAAGATTCT | 840
| TTTAAAGACA | CAGAACACTT | GTGGAATATG | TGGCAAGCCA | ATCGGATC | | 888

( 2 ) INFORMATION FOR SEQ ID NO:2:

( i ) SEQUENCE CHARACTERISTICS:
( A ) LENGTH: 265 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:2:

| | | | | | |
|---|---|---|---|---|---|
| GGATCCGTGT | CACATAACTG | AGCGCCAATA | CTTTAGAAAG | AGAAGAGCAA | TACTTGAGAA | 60
| GTATGATGAG | ATATGTGACG | GCTTCTGGTA | ATTTGTCACC | TTTTGGGCGA | AAACTGACAA | 120
| GATAAATGTT | GTATTATAGT | ATCATCAAAT | AAAACAAATA | AAGCCAGCGG | ATATATTCTG | 180
| TTGGCTTTTT | GTGTGGAGAA | AGTGAGGTGA | CCTCCCATAG | CATTACGTGC | TGACCGTACT | 240
| GGTGCGGGCT | GCAGAATTCG | ATCTG | | | | 265